United States Patent [19]

Shichman et al.

[11] Patent Number: 5,439,479
[45] Date of Patent: Aug. 8, 1995

[54] SURGICAL CLIP

[75] Inventors: Daniel Shichman, Trumbull, Conn.; Boris Zvenyatsky, Bronx, N.Y.

[73] Assignee: United States Surigcal Corporation, Norwalk, Conn.

[21] Appl. No.: 177,639

[22] Filed: Jan. 4, 1994

Related U.S. Application Data

[63] Continuation of Ser. No. 35,512, Mar. 22, 1993, abandoned, which is a continuation of Ser. No. 631,373, Dec. 20, 1990, abandoned.

[51] Int. Cl.⁶ ............................................. A61B 17/04
[52] U.S. Cl. .................................. 606/220; 606/216; 606/219; 411/452; 411/920
[58] Field of Search ............... 606/151, 216, 219, 220; 411/457, 920

[56] References Cited

U.S. PATENT DOCUMENTS

| | | | |
|---|---|---|---|
| 389,660 | 9/1888 | Mandel et al. | 24/703.4 |
| 2,881,762 | 4/1959 | Lowrie | 606/142 |
| 3,357,296 | 12/1967 | Lefever | 606/219 |
| 3,570,497 | 3/1971 | Lemole | 24/16 |
| 3,825,010 | 7/1974 | McDonald | 606/216 |
| 3,926,193 | 12/1975 | Hasson | 606/216 |
| 4,217,902 | 8/1980 | March | 606/151 |
| 4,390,019 | 6/1983 | LeVeen et al. | 606/157 |
| 4,523,591 | 6/1985 | Kaplan et al. | |
| 4,531,522 | 7/1985 | Bedi et al. | 606/220 |
| 4,532,927 | 8/1985 | Miksza, Jr. | 606/220 |
| 4,534,350 | 8/1985 | Golden et al. | 606/220 |
| 4,535,764 | 8/1985 | Ebert | |
| 4,548,202 | 10/1985 | Duncan | 606/220 |
| 4,570,623 | 2/1986 | Ellison et al. | 606/219 |
| 4,583,670 | 4/1986 | Alvarado | 227/19 |
| 4,610,250 | 9/1986 | Green | 606/220 |
| 4,627,473 | 12/1986 | Bedi et al. | 606/220 |
| 4,667,674 | 5/1987 | Korthoff et al. | 606/220 |
| 4,719,917 | 1/1988 | Barrows et al. | 606/219 |
| 4,723,540 | 2/1988 | Gilmer, Jr. | 606/219 |
| 4,724,839 | 2/1988 | Bedi et al. | 606/220 |
| 4,730,615 | 3/1988 | Sutherland et al. | |
| 4,841,960 | 6/1989 | Garner | |
| 4,887,601 | 12/1989 | Richards | 606/219 |
| 4,950,284 | 8/1990 | Green et al. | 606/216 |

FOREIGN PATENT DOCUMENTS

| | | |
|---|---|---|
| 0129442 | 6/1984 | European Pat. Off. |
| 0202090 | 5/1986 | European Pat. Off. |
| 0315344 | 10/1988 | European Pat. Off. |

Primary Examiner—Gary Jackson

[57] ABSTRACT

A surgical clip which comprises a staple having a central portion and first and second legs extending from said central portion. A retainer is provided having an opening dimensioned for passage of an end portion of each of said legs when the legs are bent from an open position to a closed position. A ratchet mechanism is provided in the form of a plurality of teeth disposed on the legs adapted to be engaged by a pawl of said retainer.

21 Claims, 4 Drawing Sheets

SURGICAL CLIP

This is a continuation of application Ser. No. 08/035,512, filed on Mar. 22, 1993, now abandoned which is a continuation of application Ser. No. 07/631,373, filed on Dec. 20, 1990 now abandoned.

BACKGROUND OF THE INVENTION

1. Field of the Invention

This invention relates to a surgical clip for closing an incision in body tissue and more particularly to a fascia clip of two piece construction comprising a staple and a retainer.

2. Description of the Related Art

Surgical fasteners have been used in surgical procedures to eliminate the need for suturing, which is both time consuming and inconvenient. In these applications the surgeon can use a fastener implanting device loaded with one or more surgical fasteners to accomplish in a few seconds what would have taken many minutes to perform by suturing. This reduction in operating time reduces blood loss and trauma to the patient.

In some applications, two part surgical fasteners are used in which the fastener is inserted at the wound site and is engaged by a retainer to hold the fastener in place. These retainers prevent the fastener from working loose from the tissue. Since the two piece fastener cannot easily be unlocked and are not easily removable, they are made of bioabsorbable material.

Possible materials for such two part fasteners include polymers and copolymers of glycolic acid (i.e. hydroxyacetic acid), the cyclic dimer of glycolic acid ("glycolide"), lactic acid, the cyclic dimer of lactic acid ("lactide") and related monomers. Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459-1464 (1979), and D. F. Williams (ed.) Biocompatibility of Clinical Implant Materials, Vol. II, ch. 9: "Biodegradable Polymers." (1981).

The use of prior fasteners and instruments has not been entirely suitable for all types of tissue. For example, many of the prior fasteners are not suitable for closing fascia tissue incisions because the tissue is relatively thick and not easily manipulated. U.S. Pat. No. 4,950,284 discloses one type of clip suitable for fascia tissue. The clip comprises a longitudinal strap which extends through an opening in the proximal end of the base and emerges through an opening at the distal end of the base.

The need exists for an improved surgical clip which can be utilized for fascia tissue, and is easy to manufacture, easy to manipulate, can be applied with accuracy, and provides a secure closure of the incision.

SUMMARY OF THE INVENTION

The present invention provides an improved surgical fascia clip for closing incisions in body tissue. The fascia clip comprises a retainer and a flexible staple having a pair of legs extending from the central portion. The legs of the staple are movable from an open position in which the legs are spaced apart and extend substantially parallel or obliquely to one another to a closed position where the legs are bent inwardly toward each other so that the end portions of the legs extend substantially parallel to the central portion of the staple and extend through an opening in the retainer. The legs may include a plurality of teeth which are engaged by a pawl disposed within the retainer to thereby improve securement of the legs within the retainer. Both the staple and the retainer are preferably and advantageously made from a bioabsorbable material.

BRIEF DESCRIPTION OF THE DRAWINGS

The present invention will be more fully appreciated as the same becomes better understood from the following detailed description of the present invention when considered in connection with the accompanying drawings in which:

FIG. 2b is an enlarged side view of the distal end portion of one of the legs of the staple of FIG. 2a;

DETAILED DESCRIPTION OF THE PREFERRED EMBODIMENTS

Figure 1:
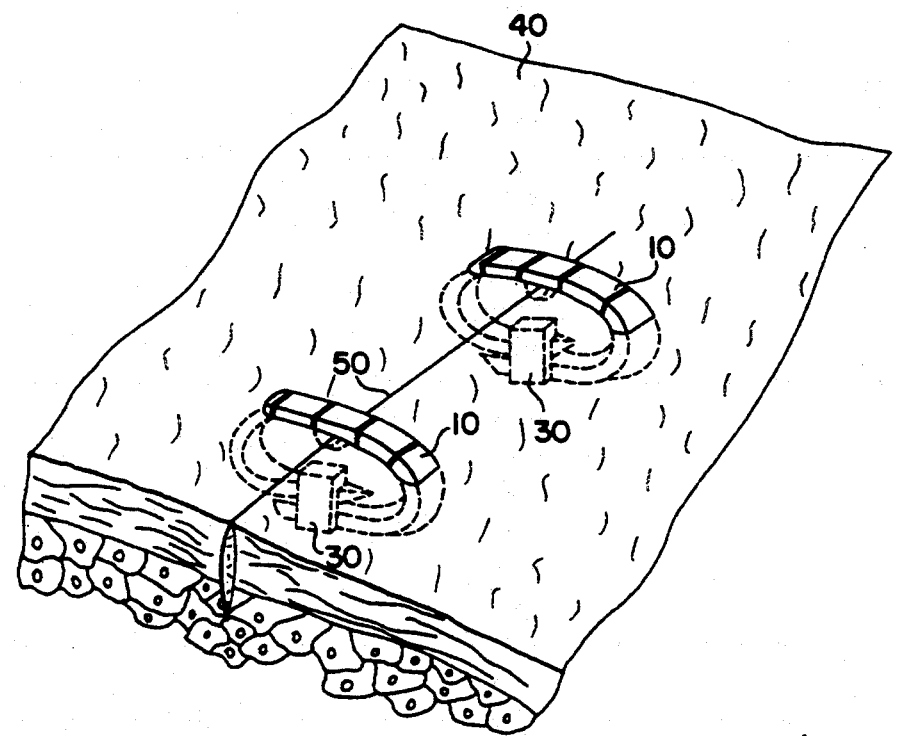
FIG. 1 illustrates a perspective view of a plurality of surgical clips of the present invention shown closing an incision in body tissue.

With reference now to the drawings, wherein like reference numerals represent identical parts throughout the several views, and more particularly to FIG. 1, a plurality of surgical clips of the present invention are shown closing an incision 50 in a layer of body tissue 40. The clips can advantageously be used to close an incision or wound in various types of tissue, including fascia tissue which is relatively thick and not easily manipulated. As illustrated, each surgical clip is of a two piece construction comprising a fastener or staple 10 and a retainer 30.

As will be described in more detail below, staple 10 is sufficiently flexible so THAT it can be bent by an appropriate instrument from an open position where the legs are spaced apart (see e.g. FIG. 2A) to a closed position where the legs are bent inwardly towards one another and extend in a direction parallel to the longitudinal axis of the central portion (see e.g. FIG. 5), thereby forming an elongated oval-shaped configuration. In the closed position as shown, the end portion of the staple legs extend through an opening in the retainer 30; the retainer thereby functions to help maintain the legs in their closed position.

Figure 2B:
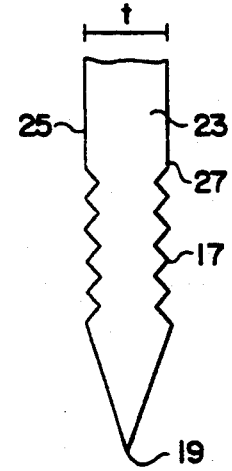
Figure 2A:
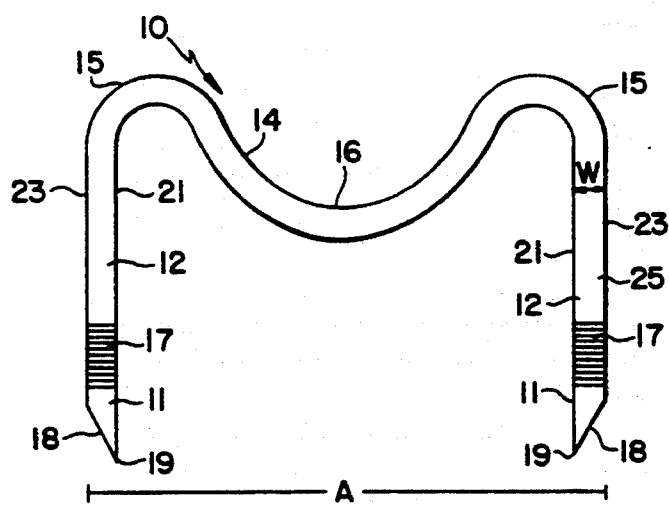
FIG. 2a illustrates a front view of the staple of the surgical clip of the present invention shown in an open position.

Referring more particularly to FIG. 2a, the staple 10 has a central portion 14 and a pair of legs 12 extending downwardly therefrom. The legs 14 are disposed substantially parallel to one another and substantially perpendicular to central portion 14. An indentation 16 is formed in central portion 14 to facilitate insertion of the staple 10 and to allow a tighter grip on the tissue held within the confined area, i.e. the oval shaped area, of the closed staple 10. Curved portions 15 are formed at the juncture of central portion 14 and legs 12 to allow bending of legs 12 to their closed position. The distal tip portion 11 of each staple leg 12 has an inclined outer surface 18 terminating in a sharp pointed tip 19 which facilitates penetration of the staple 10 into the tissue. Reference numeral 25 designates the front surface of the legs 12 and reference numerals 21 and 23 designate the inner side surface and outer side surface of the legs 12, respectively.

To improve retention of fastener legs 12 within retainer 30, a ratchet mechanism is provided in the form of a pawl disposed within the retainer adapted to engage one of the teeth formed on the staple legs. The plurality of teeth also permit the clip to automatically adjust to varying thickness of tissue. More particularly, a plurality of teeth 17 are provided at the end portion of legs 12, preferably slightly proximally of distal tip portion 11. As shown in FIG. 2B, the teeth 17 are formed in both the front and rear surfaces 25 and 27, respectively, of each leg 12 to engage opposing pawls of retainer 30 which will be described below. Although each fastener leg 12 is shown with five teeth on opposing surfaces, clearly a fewer or larger number of teeth or teeth on only one side of the leg could be provided so long as they achieve their securement and/or adjustment function. Additionally, other means can be provided to enhance securement of staple legs 12 within retainer 30 such as an interlocking mechanism.

Figure 6A:
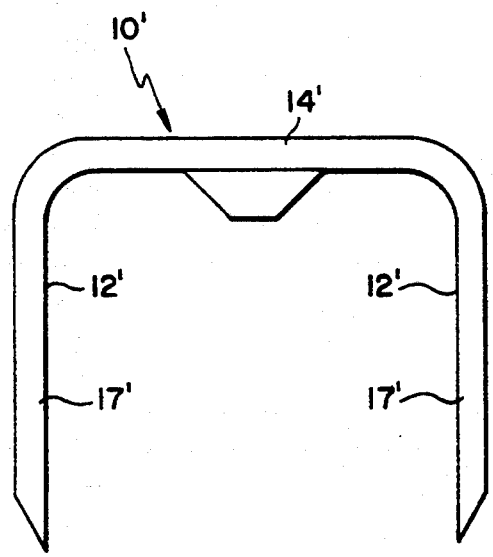
FIG. 6A illustrates a front view of an alternate embodiment of the staple of the surgical clip of the present invention.

In an alternate embodiment shown in FIG. 6A, staple 10' includes a pair of legs 12' extending substantially perpendicularly from central portion 14'. A plurality of teeth 17' are also provided. Unlike the staple 10 of FIG. 2a, the staple legs 12' are joined by a substantially linear central portion 14'. That is, there is no indentation formed in the central portion 14.

Figure 6B:
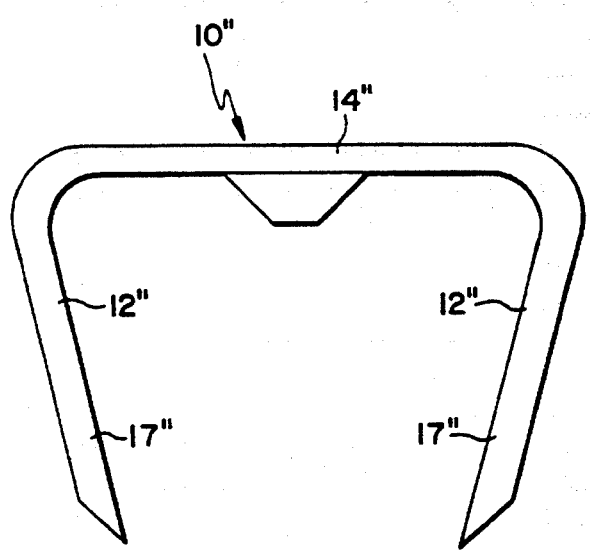
FIG. 6B illustrates a front view of another alternate embodiment of the staple of the surgical clip of the present invention.

In another alternate embodiment of the staple of the present invention shown in FIG. 6B, the staple 10" includes a pair of legs 12" extending obliquely from central portion 14". The legs are bent inwardly as in the aforementioned embodiments to engage a centrally positioned retainer. A plurality of teeth 17" are also provided proximally of the distal tip. Staple 10" can optionally include an indentation as in staple 10 of FIG. 2A.

Referring back to FIG. 2A, staple 10 has a width w, measured as the distance between interior side surfaces 21 and exterior side surfaces 23, which is preferably substantially uniform throughout its length, with the exception of tapered distal tip portion 11 which is of reduced width. The thickness t of the staple legs 12 (FIG. 2B) and of the central portion 14, measured as the distance between front surface 25 and rear surface 27, is also preferably substantially uniform and is preferably greater than width w. Clearly, the width and thickness can vary at different parts of the staple. For example, the central portion can be formed with a thickness greater than that of the legs or vice versa. Alternately, the staple legs and/or central portion can be formed of square cross section so that its width is equal to its thickness or can be formed so that its width exceeds its thickness.

In one embodiment, the length A (FIG. 2A) measured as the distance between the exterior side surfaces 23 of opposing staple legs 12 in the open position, is approximately 1.480 inches and the length B (FIG. 5), measured as the distance between the interior side surfaces 21 of opposing staple legs 12 in the closed position is approximately 0.921 inches. Clearly, these dimensions provide only an example of one of the numerous sizes in which the staples can be formed. The size of the staple as well as the ratios of width and thickness of various parts can vary depending on its particular use.

The staple 10 is preferably composed of a material which is sufficiently flexible to bend without breaking and is strong enough to provide a firm grip on the body tissue to allow healing of the incision. It is preferably composed of a bioabsorbable material such as homopolymers or copolymers of lactide, glycolide, polydioxanome, trimethyl carbonate, polythylene oxide or other bioabsorbable polymer materials or blends of these respective copolymers. One preferred material is made of a copolymer of lactide and glycolide made from approximately 18% m glycolide and 82% m lactide. Another possible bioabsorbable material for constructing the staple is disclosed in U.S. Pat. Nos. 4,523,591 to Kaplan et al, and 4,744,365 to Kaplan et al, herein incorporated by reference. Clearly, the materials disclosed in the patents and literature listed in the Background section of this application can also be utilized.

Figure 5:
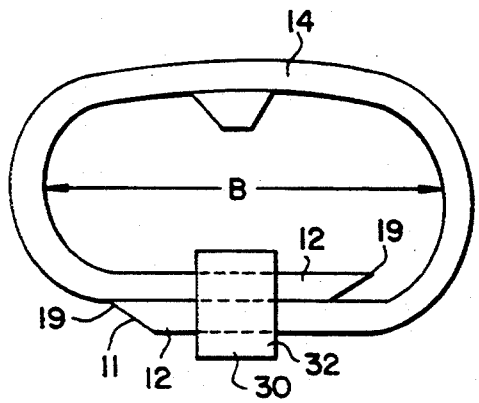
FIG. 5 illustrates a front view of the staple and retainer of the present invention showing the staple in the closed position.

Turning now to the retainer 30 of the surgical clip of the present invention, as shown in FIG. 5, the retainer 30 is positioned midway between opposing staple legs 12 and is spaced apart a sufficient distance from the central portion of staple 10 to receive the distal tip portion 11 of legs 12 when bent to the closed position.

Figure 3:
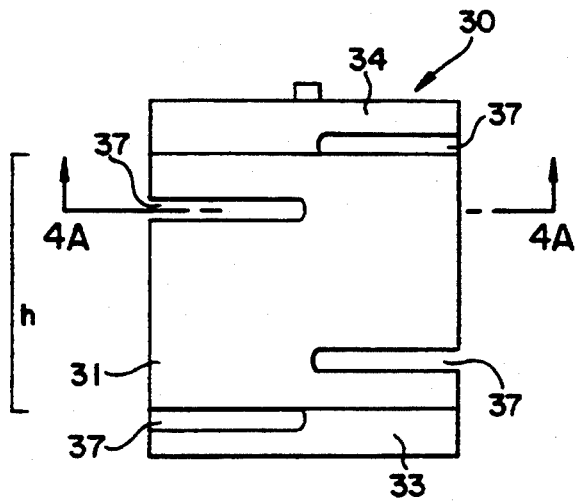
FIG. 3 illustrates a front view of the retainer of the surgical clip of the present invention.
Figure 4B:
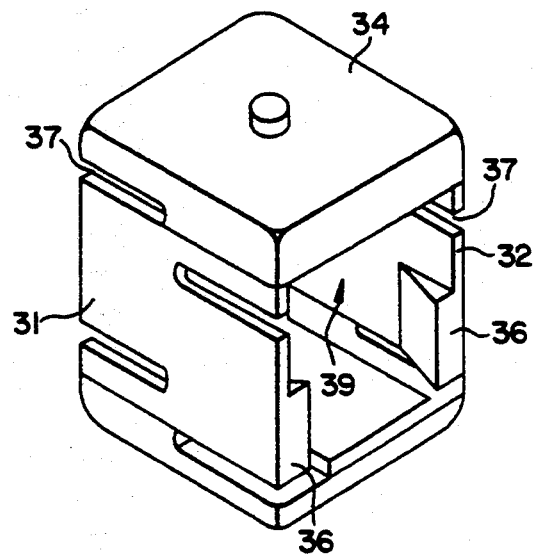
FIG. 4b illustrates a side view of the retainer of the surgical clip.
Figure 4A:
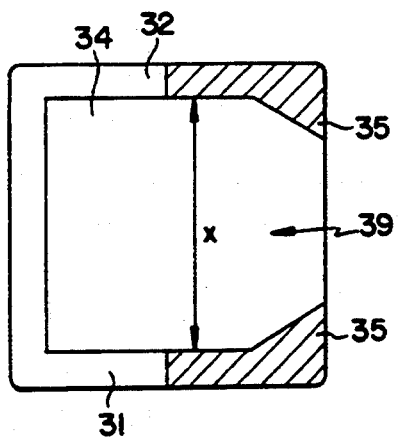
FIG. 4a is a cross-sectional view of the retainer taken along lines 4a—4a of FIG. 3.

The retainer 30, as shown in FIG. 3, has top and bottom portions 34, 33, and front and rear walls 31, 32 (FIG. 4A) positioned between the top and bottom portions. As shown, a longitudinal slot 37 is formed in both the bottom and top portions 33, 34 and two longitudinal slots are formed in the front wall 31 of the retainer 30. Similarly, two corresponding longitudinal slots are formed in rear wall 32 and in the rear surface of the bottom and top portions 33, 34. These slots maintain the resiliency of retainer 30 for the reasons explained below. The slots are illustratively shown starting at the edge of the front (or rear) wall and terminating at a midline of the retainer 30. However, clearly the slots which are preferably formed when the retainer is molded, can be formed of other configurations and in different locations and a fewer or larger number of slots can be provided.

The retainer 30 has a hollow portion forming an opening or passageway 39 extending through its entire length which is dimensioned to receive a portion of both staple legs 12. The passageway 39 is formed between top and bottom portions 34, 33 and bounded by front and rear walls 31, 32 respectively.

Protruding from the inside surface of an upper portion of both walls 31, 32 is an inwardly extending projection or pawl 35 (See FIG. 4a) which is adapted to engage the teeth 13 of one of the staple legs 12. Similarly, a pawl, designated by reference numeral 36 in FIG. 4B, protrudes from a lower portion of front and rear walls 31, 32 to engage opposing teeth 17 of the other staple leg 12. The passageway 39 is preferably dimensioned to have a height h, measured as the distance between top portion 34 and bottom portion 33 (see FIG. 3), slightly less than the combined thickness t of the legs 12 and a width x, measured as the distance between front wall 31 and rear wall 32 (FIG. 4a), slightly less than the width w of each staple leg 12. These dimensions advantageously result in the resilient retainer walls being slightly expanded when the legs 12 are inserted through passageway 39 and then springing back due to their resiliency to more tightly grasp the legs. Clearly, the relationship of the dimensions of the passageway 39 and the staple legs 12 will vary depending on the configuration of the legs in the closed position as will become apparent from the discussion below.

The retainer is preferably made of a copolymer of lactide and glycolide made from approximately 18% m glycolide and 82% m lactide. Other possible bioabsorbable materials include those discussed above with respect to the staple 10.

Turning now to the closed configuration of staple 10, and more particularly to FIG. 5, legs 12 are bent into their closed position so that they extend through passageway 39 of retainer 30. As illustrated, retainer 30 is positioned distally of central portion 14 and centered with respect thereto. Each staple leg 12 enters through one side of passageway 39, extends through the entire length of the passageway, and emerges from the opposite side. Thus, a distal portion of each leg 12 extends beyond the edges of front and rear walls 31, 32. In an alternate embodiment shown in FIG. 7, the legs 12 extend into, but not beyond, the passageway 39 of retainer 30 so that the distal end portions of legs 12 terminate within retainer 20. The central portion 14 in both embodiments is substantially linear in the closed position as movement of staple legs 12 straighten central portion 14 to thereby remove the indentation 16.

Figure 7:
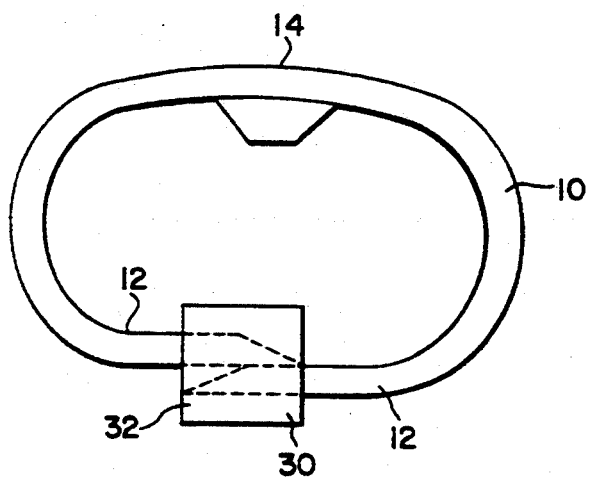
FIG. 7 illustrates a front view of an alternate embodiment of the staple and retainer of the present invention showing the staple in the closed position.

In the embodiment shown in FIGS. 5 and 7, the closed staple legs 12 are positioned one atop the other and in abutting relationship. However, alternatively, the legs can be spaced apart from one another in the closed position. In such configuration, a separate passageway can optionally be provided for each staple leg. In another alternate embodiment, the staple legs can be arranged in side-by-side relationship within the passageway rather than above one another. The retainer 30 and passageway 39 would be appropriately dimensioned to accommodate this configuration.

Figure 8:
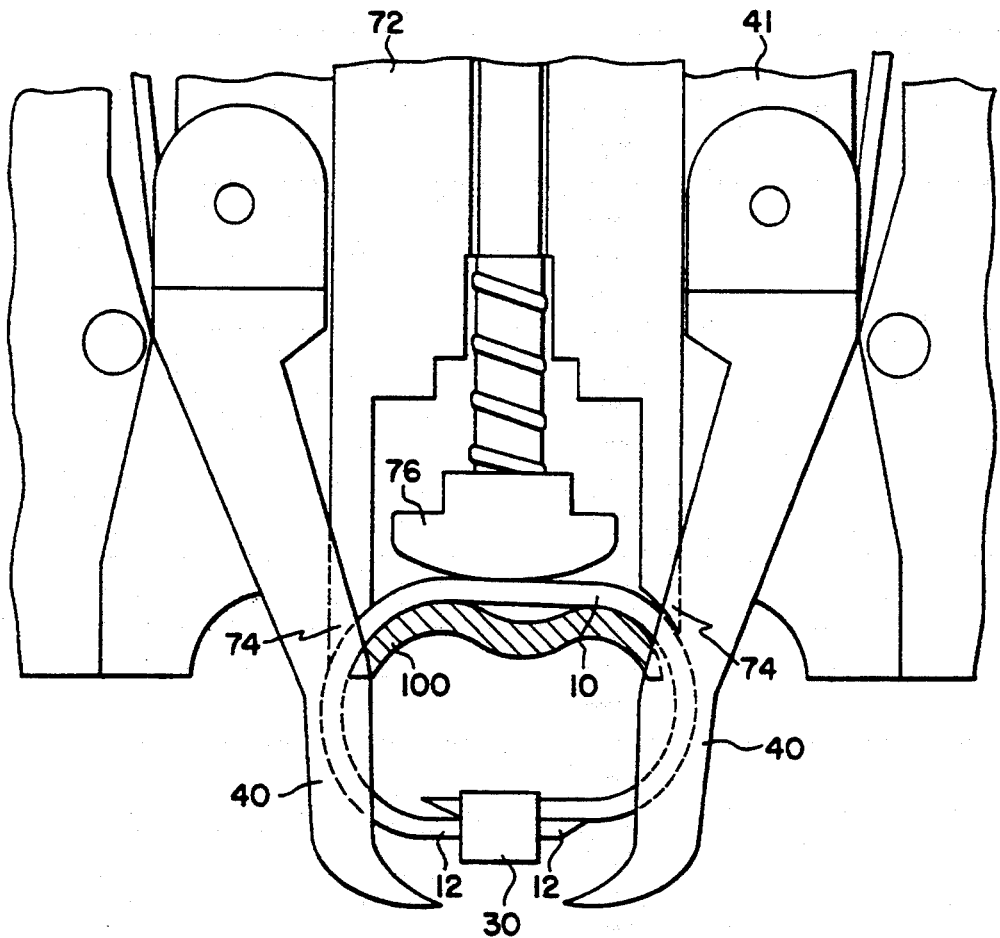
FIG. 8 illustrates an apparatus for applying the surgical clip of the present invention.

The surgical clip of the present invention is applied to body tissue by means of a suitable apparatus. FIG. 8 illustrates the components of one such apparatus which can be utilized to apply the clips and comprises a pair of approximators 40 configured to both grasp the body tissue and to bend the staple legs, a pusher 42 having spaced apart fingers 44 to engage and push staple 10 distally, and an alignment member 46 to engage the central portion or indentation of the staple 10 to facilitate centering of the staple.

In use, to close an incision in fascia tissue, the approximators 40, which are pivotally mounted to the apparatus housing (not shown), are each placed on an opposing side of the incision and inserted into the tissue. Such placement of the approximators 40 likewise results in the centering of the staple 10 above the incision. The approximators 40 are then pivoted inwardly, thereby pulling the two tissue portions on opposing sides of the incision towards each other. Retainer 20 is guided by any suitable means, such as a ramp, (not shown), to a distal position underneath the incision (below the top surface of the tissue) and transversely centered with respect to the incision. The pusher 42 is actuated and moves forwardly so that the staple engaging fingers 44 press against the juncture between the central portion 14 and legs 12 (adjacent curved portion 15) to move staple 10 distally. Distal movement of staple 10 results in contact with the inner surface of approximators 40 which force the legs 12 inwardly toward one another. Continued distal movement causes further inward bending of the legs 12 which allows them to pass through opposite sides of the passageway 39 of retainer 30. When inward bending is complete i.e. the staple is forced to its closed position, the appropriate tooth 17 located at the distal end portion of the legs 12 is engaged and secured by the pawl of the retainer 30 to thereby help prevent withdrawal of the legs from the retainer passageway 39. As a result, the staple 12 and retainer 30 form a substantially continuous, e.g. oval, enclosure around the incision, thereby ensuring a firm grip on the fascia tissue and a secure closure around the incision. After the clip is applied, the pusher 42 is retracted and the approximators 40 are rotated outwardly and removed from the tissue leaving the clip firmly in place. As shown in FIG. 1, a plurality of clips can be inserted along the length of the incision by moving the apparatus to a new position along the incision and applying a new clip in the manner described above.

It will be understood that the foregoing is illustrative of the principles of the invention and that various modifications can be made by those skilled in the art without departing from the scope and spirit of the present invention.

What is claimed is:

1. A surgical clip assembly, comprising:
 a staple having a central portion and first and second legs extending from said central portion, each said leg having gripping means;
 a retainer spaced apart from said central portion and having a central opening dimensioned for passage and retention of an end portion of both said legs, every dimension of said retainer being less than the length of said staple central portion, the length of said staple central portion being measured as the distance between the exterior side surfaces of said staple legs in the open position; and
 means or said retainer for engaging said gripping means to retain said end portion of said legs in said retainer.

2. A surgical clip assembly as recited in claim 1, wherein said gripping means comprises at least one tooth.

3. A surgical clip assembly as recited in claim 2, wherein said holding means comprise a pawl configured to engage said at least one tooth.

4. A surgical clip assembly as recited in claim 1, wherein said staple and retainer are composed of a resorbable material.

5. A surgical clip assembly as recited in claim 4, wherein said staple and retainer are composed of a material selected from the group consisting of polyglycolide, polylactide and glycolide/lactide copolymer.

6. A surgical clip assembly as recited in claim 1, wherein said retainer is made of a resilient material and dimensioned to stretch upon insertion of said legs and spring back to its original position after such insertion.

7. A surgical clip assembly as recited in claim 6, wherein said retainer comprises a plurality of slots to maintain resiliency.

8. A surgical clip assembly as recited in claim 1, wherein said legs are retained in overlaying abutting relationship.

9. A surgical clip assembly comprising:
   a staple having a central portion and first and second legs extending from said central portion, each leg having gripping means formed thereon; and
   a retainer spaced apart from said central portion, every dimension of said retainer being less than the greatest length of said staple central portion, said retainer having a passageway dimensioned to receive said first and second legs and further having holding means to secure said legs therewithin.

10. A surgical clip assembly as recited in claim 9, wherein said holding means comprises an upper pawl disposed on an upper inside surface and a lower pawl disposed on a lower inside surface, said upper pawl engaging said first leg portion when inserted in a first direction through said passageway and said lower pawl engaging said second leg portion when inserted in a second direction through said passageway.

11. A surgical clip assembly comprising:
   a staple having a central portion and a pair of legs joined at a proximal end by said central portion, said legs each having an outer edge and a distal end portion and further being movable from an open position in which said legs are spaced apart to a closed position wherein said legs are bent at an angle to extend inwardly towards each other; and
   a retainer having an opening to receive said legs when in said closed position, every dimension of said retainer having a length less than the distance between the exterior side surfaces of the staple legs in said open position, said retainer receiving said legs only in a direction substantially parallel to said central portion.

12. A surgical clip assembly as recited in claim 11, wherein said retainer is made of a resilient material and dimensioned to stretch upon insertion of said legs and spring back after such insertion.

13. A surgical clip assembly as recited in claim 12, wherein said clip further comprises a ratchet mechanism to retain said distal end portions of said legs within said retainer.

14. A surgical clip assembly as recited in claim 13, wherein in said second position one of said legs is disposed above the other leg.

15. A surgical clip assembly as recited in claim 14, wherein the height of said opening of said retainer is less than the combined thickness of said distal end portions of said legs.

16. A surgical clip assembly as recited in claim 15, wherein the width of said opening is less than the width of each of said legs.

17. A surgical clip assembly as recited in claim 14, wherein in said second position a lower surface of said first leg abuts an upper surface of said second leg.

18. A surgical clip assembly as recited in claim 16, wherein said ratchet mechanism comprises a plurality of teeth disposed proximally of a distal tip of each of said legs and has a lower pawl to engage said teeth of said first leg and an upper pawl to engage said teeth of said second leg.

19. A surgical clip assembly as recited in claim 13, wherein said legs enter through one end of said opening and emerge from the opposite end of said opening.

20. A surgical staple as recited in claim 11, wherein in said closed position, the distal end portion of each of said legs is substantially parallel to said central portion of said staple.

21. A surgical clip assembly comprising:
   a staple having a central portion and first and second legs extending from said central portion to a first and second distal end portion, said legs being flexible to move from an open position to a closed position; and
   a retainer having at least one passageway extending substantially parallel to said central portion and dimensioned to receive said legs when moved inwardly to said closed position, wherein when said staple legs are deformed to said closed position, said retainer contacts only those portions of said staple legs which are in substantial parallel alignment with said staple central portion.

* * * * *